United States Patent
Scheer et al.

(10) Patent No.: US 7,444,196 B2
(45) Date of Patent: Oct. 28, 2008

(54) OPTIMIZED CHARACTERIZATION OF WAFERS STRUCTURES FOR OPTICAL METROLOGY

(75) Inventors: Steven Scheer, Austin, TX (US); Alan Nolet, San Jose, CA (US); Manuel Madriaga, San Jose, CA (US)

(73) Assignee: Timbre Technologies, Inc., Santa Clara, CA (US)

( * ) Notice: Subject to any disclaimer, the term of this patent is extended or adjusted under 35 U.S.C. 154(b) by 368 days.

(21) Appl. No.: 11/408,744

(22) Filed: Apr. 21, 2006

(65) Prior Publication Data

US 2007/0250200 A1 Oct. 25, 2007

(51) Int. Cl.
- G06F 19/00 (2006.01)
- G01B 11/14 (2006.01)
- G01R 31/26 (2006.01)
- H01L 21/66 (2006.01)

(52) U.S. Cl. .............. 700/109; 700/108; 700/121; 430/311; 430/312; 430/313; 430/315; 430/321; 356/305; 356/326; 356/328

(58) Field of Classification Search .............. 700/108, 700/109, 121; 356/305, 326, 328; 430/311–316, 430/321

See application file for complete search history.

(56) References Cited

U.S. PATENT DOCUMENTS

| | | |
|---|---|---|
| 6,462,817 B1 | 10/2002 | Strocchia-Rivera |
| 6,647,137 B1 * | 11/2003 | Lu .............................. 382/144 |
| 6,650,957 B1 * | 11/2003 | Campbell et al. ........... 700/121 |
| 6,701,512 B2 * | 3/2004 | Sutani et al. ................... 716/21 |
| 6,704,920 B2 * | 3/2004 | Brill et al. ...................... 716/19 |
| 6,792,328 B2 * | 9/2004 | Laughery et al. ............. 700/121 |
| 6,868,301 B1 * | 3/2005 | Preil ........................... 700/121 |
| 6,871,337 B2 * | 3/2005 | Socha .......................... 716/19 |
| 6,913,900 B2 | 7/2005 | Kaplan et al. |
| 7,038,222 B1 * | 5/2006 | Budri et al. .............. 250/492.2 |
| 7,065,423 B2 * | 6/2006 | Prager et al. ................. 700/108 |
| 7,171,284 B2 * | 1/2007 | Vuong et al. ................. 700/121 |
| 7,212,282 B2 * | 5/2007 | Hau-Riege ................ 356/237.5 |
| 7,221,989 B2 * | 5/2007 | Prager et al. ................. 700/108 |
| 7,324,193 B2 * | 1/2008 | Lally et al. ................ 356/237.2 |
| 7,327,475 B1 * | 2/2008 | Chu et al. ..................... 356/625 |

(Continued)

OTHER PUBLICATIONS

"Patterned multiple color polymer light-emmitting diodes", Bao et al, Bell Laborotories, Lucent Technologies, 1999 Elsevier Sciences S.A.*

(Continued)

*Primary Examiner*—Michael D Masinick
(74) *Attorney, Agent, or Firm*—Morrison & Foerster LLP

(57) ABSTRACT

A patterned structure in a wafer is created using one or more fabrication treatment processes. The patterned structure has a treated and an untreated portion. One or more diffraction sensitivity enhancement techniques are applied to the structure, the one or more diffraction sensitivity enhancement techniques adjusting one or more properties of the patterned structure to enhance diffraction contrast between the treated portion and untreated portions. A first diffraction signal is measured off an unpatterned structure on the wafer using an optical metrology device. A second diffraction signal is measured off the patterned structure on the wafer using the optical metrology device. One or more diffraction sensitivity enhancement techniques are selected based on comparisons of the first and second diffraction signals.

32 Claims, 12 Drawing Sheets

U.S. PATENT DOCUMENTS

| | | | |
|---|---|---|---|
| 7,355,728 B2* | 4/2008 | Li et al. | 356/625 |
| 7,373,216 B1* | 5/2008 | Winkler et al. | 700/121 |
| 2002/0072003 A1* | 6/2002 | Brill et al. | 430/30 |
| 2004/0017574 A1 | 1/2004 | Vuong | |
| 2004/0267397 A1* | 12/2004 | Doddi et al. | 700/110 |
| 2005/0209816 A1 | 9/2005 | Vuong | |
| 2006/0009872 A1* | 1/2006 | Prager et al. | 700/121 |
| 2007/0135959 A1* | 6/2007 | Vuong et al. | 700/121 |
| 2007/0225851 A1* | 9/2007 | Prager et al. | 700/108 |
| 2007/0233305 A1* | 10/2007 | Werkman et al. | 700/121 |
| 2007/0250200 A1* | 10/2007 | Scheer et al. | 700/109 |
| 2008/0073114 A1* | 3/2008 | Kosowsky et al. | 174/262 |

OTHER PUBLICATIONS

"Ultraviolet and direct ultraviolet inspection of next generation lithography reticles*", Pettibone et al, KLA-Tencor; Rapid Division, J. Vac Sci Techno. B 20(6), Nov./Dec. 2002. American Vacuum Society.*

Cameron et al., "Photoacid Generation in Chemically Amplified Resists: Elucidation of Structural Effects of Photoacid Generators using New Acid Sensitive Dyes for Monitoring Acid Generation," *SPIE*, 3333: 680-691.

Haykin, S., (1999) *Neural Networks*, Prentice Hall.

Ichimura, K. et al., (2004) "Photoacid-catalysed pigmentation of dyestuff precursors enhanced by acid amplifiers in polymer films," *J. Mater. Chem.*, 14:1164-1172.

* cited by examiner

OPTIMIZED CHARACTERIZATION OF WAFERS STRUCTURES FOR OPTICAL METROLOGY

BACKGROUND

1. Field

The present application generally relates to optical metrology, and, more particularly, to optimizing the diffraction characteristics of wafer structures for optical metrology.

2. Related Art

In semiconductor manufacturing, periodic gratings are typically used for quality assurance. For example, one typical use of periodic gratings includes fabricating a periodic grating in proximity to the operating structure of a semiconductor chip. The periodic grating is then illuminated with an electromagnetic radiation. The electromagnetic radiation that deflects off of the periodic grating are collected as a diffraction signal. The diffraction signal is then analyzed to determine whether the periodic grating, and by extension whether the operating structure of the semiconductor chip, has been fabricated according to specifications.

In one conventional system, the diffraction signal collected from illuminating the periodic grating (the measured-diffraction signal) is compared to a library of simulated-diffraction signals. Each simulated-diffraction signal in the library is associated with a hypothetical profile. When a match is made between the measured-diffraction signal and one of the simulated-diffraction signals in the library, the hypothetical profile associated with the simulated-diffraction signal is presumed to represent the actual profile of the periodic grating.

The library of simulated-diffraction signals can be generated using a rigorous method, such as rigorous coupled wave analysis (RCWA). More particularly, in the diffraction modeling technique, a simulated-diffraction signal is calculated based, in part, on solving Maxwell's equations. Calculating the simulated diffraction signal involves performing a large number of complex calculations, which can be time consuming and costly.

At various points of the wafer processing, it is desirable to measure the structure before, during, and/or after a fabrication process. For example, after exposure of the resist and prior to stripping away the unexposed resist in photolithography, there is a need to measure the structure in order to predict if the exposure step was performed within the processing window for the recipe. The difficulty of making a successful measurement is that the exposed and unexposed resist have very similar optical properties. Another example is the need to measure the structure while development of a previously exposed resist is ongoing. The information about the structure profile obtained while development of the resist is in process can be used to control the resist development or adjust a process variable in the fabrication cluster.

SUMMARY

In one exemplary embodiment, a patterned structure in a wafer is created using one or more fabrication treatment processes wherein the patterned structure has a treated and an untreated portion. One or more diffraction sensitivity enhancement techniques are applied to the structure, the one or more diffraction sensitivity enhancement techniques adjusting one or more properties of the patterned structure to enhance diffraction contrast between the treated portion and untreated portions. A first diffraction signal is measured off an unpatterned structure on the wafer using an optical metrology device. A second diffraction signal is measured off the patterned structure on the wafer using the optical metrology device. One or more diffraction sensitivity enhancement techniques is selected based on comparisons of the first and second diffraction signals.

DETAILED DESCRIPTION OF EXEMPLARY EMBODIMENT(S)

In order to facilitate the description of the present invention, a semiconductor wafer may be utilized to illustrate an application of the concept. The methods and processes equally apply to other work pieces that have repeating structures. Furthermore, in this application, the terms diffraction signal sensitivity enhancement and optical sensitivity enhancement mean the same thing and are used interchangeably.

Figure 1A:
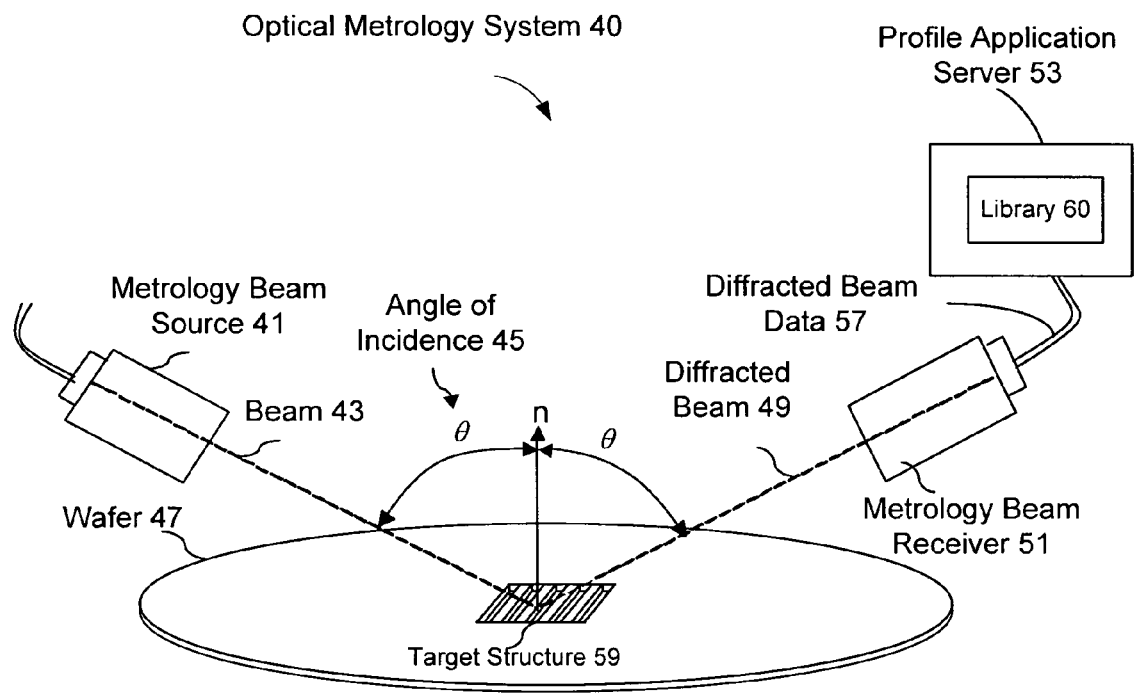
FIG. 1A is an architectural diagram illustrating an exemplary embodiment where optical metrology can be utilized to determine the profiles of structures on a semiconductor wafer.

FIG. 1A is an architectural diagram illustrating an exemplary embodiment where optical metrology can be utilized to determine the profiles of structures on a semiconductor wafer. The optical metrology system 40 includes a metrology beam source 41 projecting a beam 43 at the target structure 59 of a wafer 47. The metrology beam 43 is projected at an incidence angle θ towards the target structure 59. The diffraction beam 49 is measured by a metrology beam receiver 51. The diffraction beam data 57 is transmitted to a profile application server 53. The profile application server 53 compares the measured diffraction beam data 57 against a library 60 of simulated diffraction beam data representing varying combinations of critical dimensions of the target structure and resolution. In one exemplary embodiment, the library 60 instance best matching the measured diffraction beam data 57 is selected. It is understood that although a library of diffraction spectra or signals and associated hypothetical profiles is frequently used to illustrate concepts and principles, the present invention equally applies to a data space comprising simulated diffraction signals and associated set of profile parameters, such as in regression, neural net, and similar methods used for profile extraction. The hypothetical profile and associated critical dimensions of the selected library 60 instance is assumed to correspond to the actual cross-sectional profile and critical dimensions of the features of the target structure 59. The optical metrology system 40 may utilize a reflectometer, an ellipsometer, or other optical metrology device to measure the diffraction beam or signal. An optical metrology system is described in U.S. Pat. No. 6,913,900, entitled GENERATION OF A LIBRARY OF PERIODIC GRATING DIFFRACTION SIGNAL, by Niu, et al., issued on Sep. 13, 2005, and is incorporated in its entirety herein by reference. Other exemplary embodiments of the present invention in optical metrology not requiring the use of libraries are discussed below.

An alternative is to generate the library of simulated-diffraction signals using a machine learning system (MLS). Prior to generating the library of simulated-diffraction signals, the MLS is trained using known input and output data. In one exemplary embodiment, simulated diffraction signals can be generated using a machine learning system (MLS) employing a machine learning algorithm, such as back-propagation, radial basis function, support vector, kernel regression, and the like. For a more detailed description of machine learning systems and algorithms, see "Neural Networks" by Simon Haykin, Prentice Hall, 1999, which is incorporated herein by reference in its entirety. See also U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

Figure 1B:
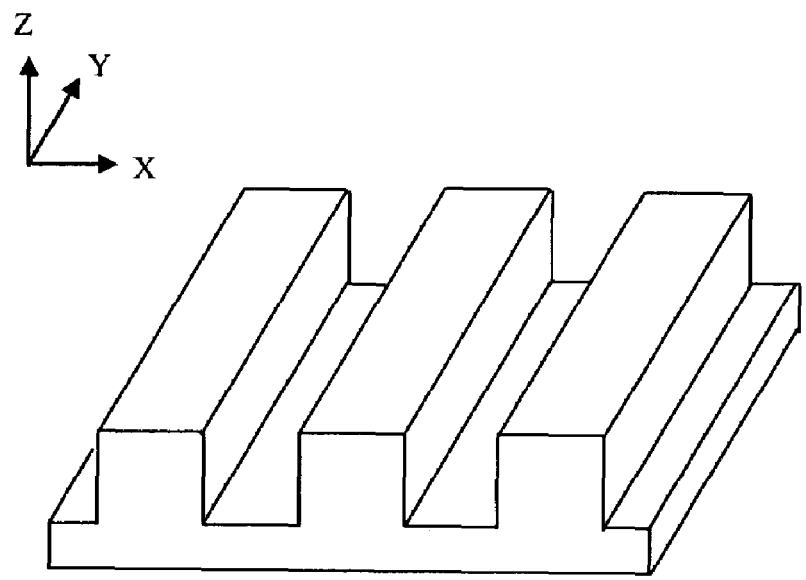
FIG. 1B depicts an exemplary one-dimensional repeating structure.

The term "one-dimensional structure" is used herein to refer to a structure having a profile that varies in one dimension. For example, FIG. 1B depicts a periodic grating having a profile that varies in one dimension (i.e., the x-direction). The profile of the periodic grating depicted in FIG. 1B varies in the z-direction as a function of the x-direction. However, the profile of the periodic grating depicted in FIG. 1B is assumed to be substantially uniform or continuous in the y-direction.

Figure 1C:
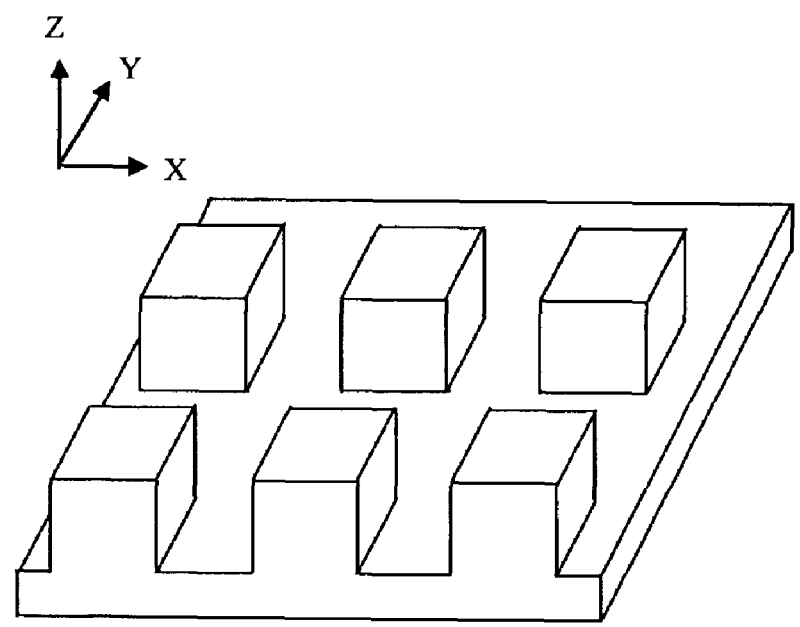
FIG. 1C depicts an exemplary two-dimensional repeating structure

The term "two-dimensional structure" is used herein to refer to a structure having a profile that varies in two-dimensions. For example, FIG. 1C depicts a periodic grating having a profile that varies in two dimensions (i.e., the x-direction and the y-direction). The profile of the periodic grating depicted in FIG. 1C varies in the z-direction.

Figure 2A:
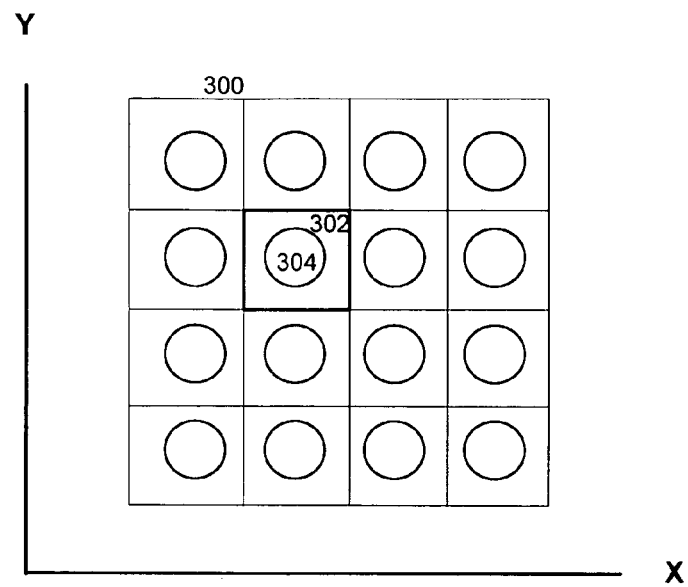
FIG. 2A depicts exemplary orthogonal grid of unit cells of a two-dimensional repeating structure.

Discussion for FIGS. 2A, 2B, and 2C below describe the characterization of two-dimensional repeating structures for optical metrology modeling. FIG. 2A depicts a top-view of exemplary orthogonal grid of unit cells of a two-dimensional repeating structure. A hypothetical grid of lines is superimposed on the top-view of the repeating structure where the lines of the grid are drawn along the direction of periodicity. The hypothetical grid of lines forms areas referred to as unit cells. The unit cells may be arranged in an orthogonal or non-orthogonal configuration. Two-dimensional repeating structures may comprise features such as repeating posts, contact holes, vias, islands, or combinations of two or more shapes within a unit cell. Furthermore, the features may have a variety of shapes and may be concave or convex features or a combination of concave and convex features. Referring to FIG. 2A, the repeating structure 300 comprises unit cells with holes arranged in an orthogonal manner. Unit cell 302 includes all the features and components inside the unit cell 302, primarily comprising a hole 304 substantially in the center of the unit cell 302.

Figure 2B:
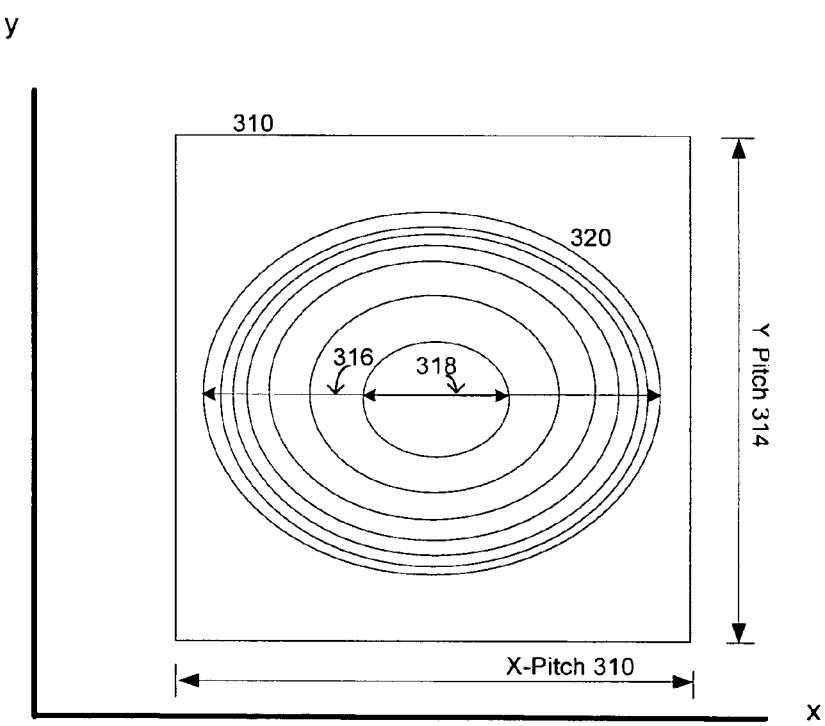
FIG. 2B depicts a top-view of a two-dimensional repeating structure.

FIG. 2B depicts a top-view of a two-dimensional repeating structure. Unit cell 310 includes a concave elliptical hole. FIG. 2B shows a unit cell 310 with a feature 320 that comprises an elliptical hole wherein the dimensions become progressively smaller until the bottom of the hole. Profile parameters used to characterize the structure includes the X-pitch 310 and the Y-pitch 314. In addition, the major axis of the ellipse 316 that represents the top of the feature 320 and the major axis of the ellipse 318 that represents the bottom of the feature 320 may be used to characterize the feature 320. Furthermore, any intermediate major axis between the top and bottom of the feature may also be used as well as any minor axis of the top, intermediate, or bottom ellipse, (not shown).

Figure 2C:
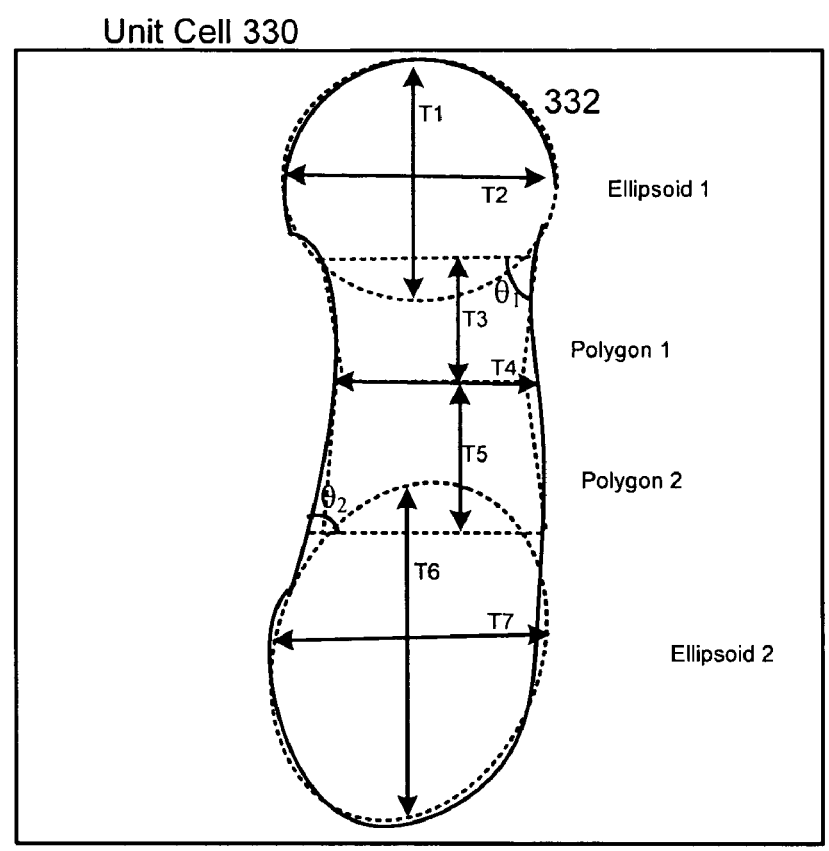
FIG. 2C is an exemplary technique for characterizing the top-view of a two-dimensional repeating structure.

FIG. 2C is an exemplary technique for characterizing the top-view of a two-dimensional repeating structure. A unit cell 330 of a repeating structure is a feature 332, an island with a peanut-shape viewed from the top. One modeling approach includes approximating the feature 332 with a variable number or combinations of ellipses and polygons. Assume further that after analyzing the variability of the top-view shape of the feature 322, it was determined that two ellipses, Ellipsoid 1 and Ellipsoid 2, and two polygons, Polygon 1 and Polygon 2 were found to fully characterize feature 332. In turn, parameters needed to characterize the two ellipses and two polygons comprise nine parameters as follows: T1 and T2 for Ellipsoid 1; T3, T4, and $\theta_1$ for Polygon 1; T4, T5, and $\theta_2$ for Polygon 2; T6 and T7 for Ellipsoid 2. Many other combinations of shapes could be used to characterize the top-view of the feature 332 in unit cell 330. For a detailed description of modeling two-dimensional repeating structures, refer to U.S. patent application Ser. No. 11/061,303, OPTICAL METROLOGY OPTIMIZATION FOR REPETITIVE STRUCTURES, by Vuong, et al., filed on Apr. 27, 2004, and is incorporated in its entirety herein by reference.

Figure 3:
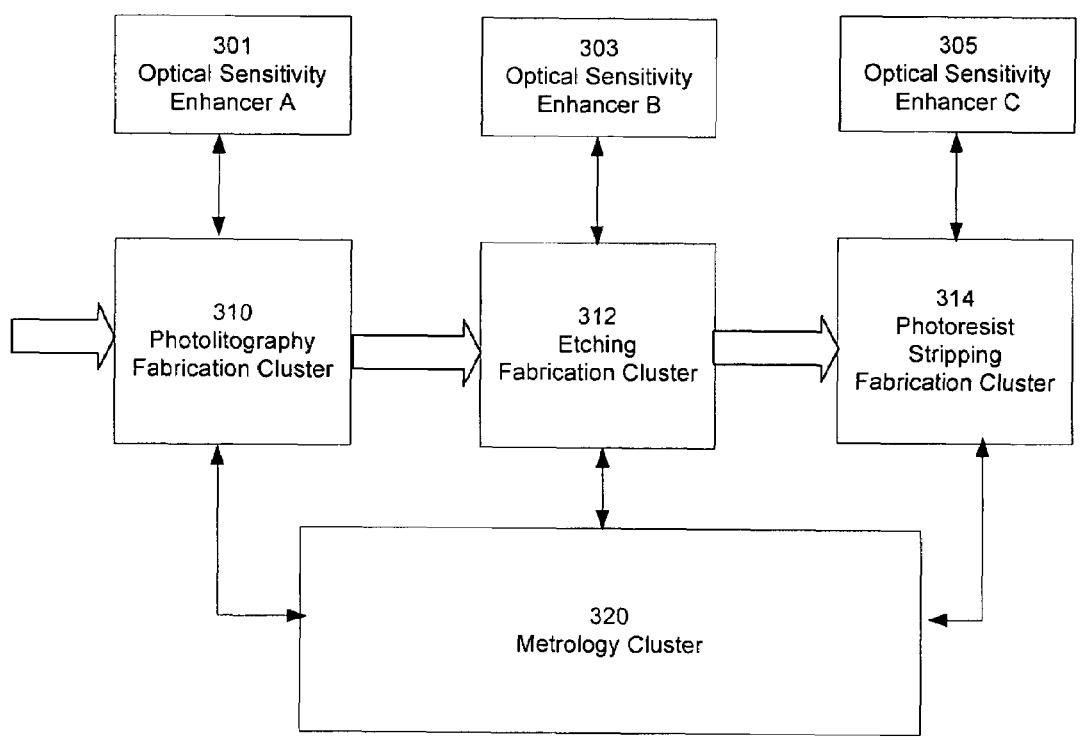
FIG. 3 is an architectural diagram of a fabrication process depicting optical sensitivity enhancement of wafer structures for optical metrology.

FIG. 3 is an architectural diagram of a fabrication process depicting optical sensitivity enhancement of wafer structures for optical metrology. Fabrication treatment processes include photolithography, etching, stripping, thermal processes, and the like. The term treated refers to portions of the wafer structures affected by a fabrication treatment process. The term untreated refers to portions of the wafer structures that are not affected by the fabrication treatment process. For example, as mentioned above in the photolithography example, the treated portion is the portion exposed to the light and the untreated portion is the unexposed portion where the mask prevented exposure to the light.

Referring to FIG. 3, a photolithography fabrication cluster unit 310 processes input wafers (not shown), using an optical sensitivity enhancer A 301, and measures the wafer structures using metrology cluster 320. The optical sensitivity enhancer A 301 comprises one or more devices that can adjust the properties or material content of the structure such that the treated and untreated portions of the structure provide different diffraction characteristics. More specifically, the optical sensitivity enhancer A 301 may be a separate device or may reside in the photolithographic fabrication cluster 310 where the diffraction characteristics of the exposed and unexposed portion of the resist are enhanced for one or more type of metrology devices in the metrology cluster 320. The metrology cluster 320 may include scatterometry devices such as ellipsometers, reflectometers, and the like.

Referring to FIG. 3, after the wafer completes the processing steps in the photolithography fabrication cluster unit 310, optical sensitivity enhancer A 301, and the metrology cluster 320, the wafer proceeds to the etching fabrication cluster 312. At one point in the series of processing steps in the etching fabrication cluster 312, an optical sensitivity enhancer B 303 is used to enhance the diffraction sensitivity of the wafer structure and the wafer structure is measured using metrology cluster 320. The optical sensitivity enhancer B 303 comprises one or more devices that can adjust the properties or material content of the structure such that the treated and untreated portions of the structure provide different diffraction characteristics. More specifically, the optical sensitivity enhancer B 303 may be a separate device or may reside in the etch fabrication cluster 312 where the diffraction characteristics of the treated and untreated portions of the structure are enhanced for one or more type of metrology devices in the metrology cluster 320. As mentioned above, the metrology cluster 320 may include scatterometry devices such as ellipsometers, reflectometers, and the like.

Still referring to FIG. 3, after the wafer completes the processing steps in the etch fabrication cluster unit 312, optical sensitivity enhancer B 303, and the metrology cluster 320, the wafer proceeds to the photoresist stripping fabrication cluster 314. At one point in the series of processing steps in the stripping fabrication cluster 314, an optical sensitivity enhancer C 305 is used to enhance the diffraction sensitivity of the wafer structure, and the wafer structure is measured using metrology cluster 320. The optical sensitivity enhancer C 305 comprises one or more devices that can adjust the properties or material content of the structure such that the treated and untreated portions of the structure provide different diffraction characteristics. More specifically, the optical sensitivity enhancer C 305 may be a separate device or may reside in the fabrication cluster where the diffraction characteristics of the exposed and unexposed portion of the structure are enhanced for one or more type of metrology devices in the metrology cluster 320. As mentioned above, the metrology cluster 320 may include scatterometry devices such as ellipsometers, reflectometers, and the like. Furthermore, the metrology cluster 320 may be a one or several metrology cluster units, where the photolithography cluster 310, the etching cluster 312, and the photoresist stripping cluster 314 each have it separate set of metrology devices.

Figure 4:
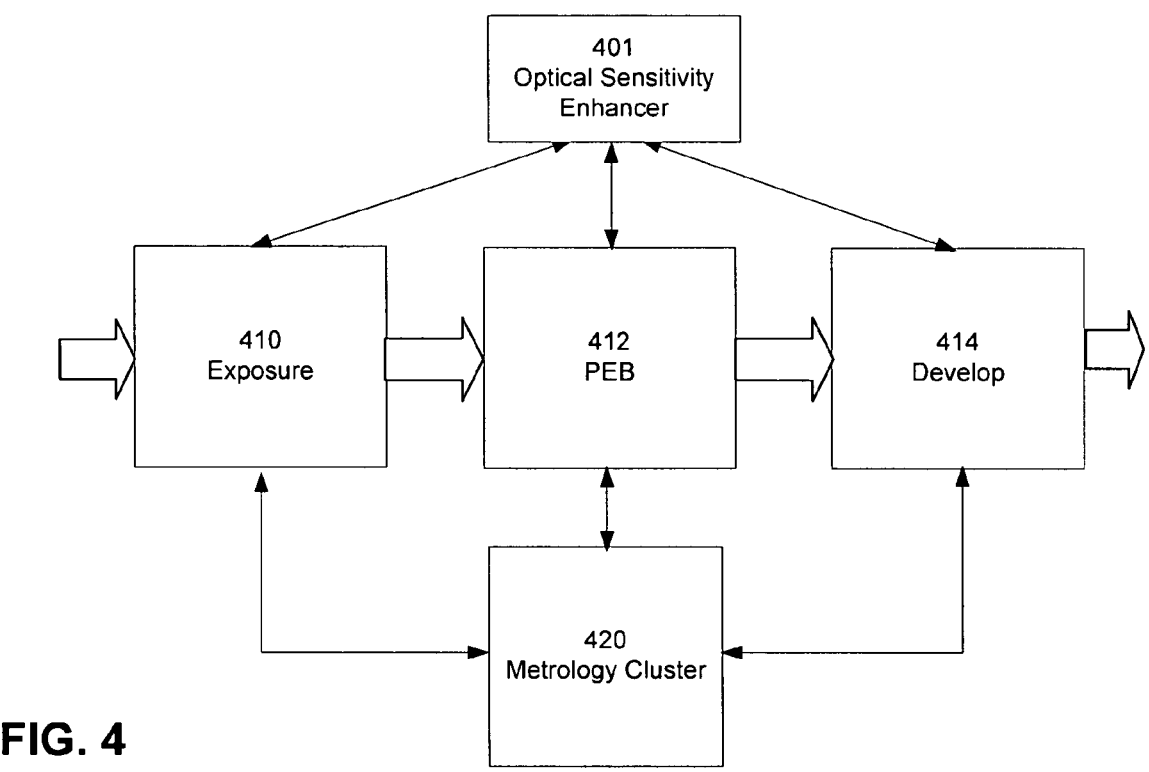
FIG. 4 is an architectural diagram of a photolithography fabrication process depicting optical sensitivity enhancement of wafer structures for optical metrology.

FIG. 4 is an architectural diagram of a photolithography fabrication process depicting optical sensitivity enhancement of wafer structures for optical metrology. In a photolithography fabrication process, the photolithography cluster 310 depicted as in FIG. 3 is further detailed showing several separate steps in FIG. 4. After the exposure process 410 step, the structure undergoes a diffraction enhancement in the optical sensitivity enhancer 401. As mentioned earlier, diffraction enhancement may be done by altering the content or diffraction properties of either the exposed or unexposed portion of the resist. In one embodiment, a molecule or compound is used to enhance the diffraction properties of the exposed resist. The molecule causes a change in absorption when exposed to acid such as the acid generated during the photo-acid generation (PAG) after the exposure of the resist. There are several molecules that achieve this goal of diffraction enhancement. In general, a molecule or compound that is useful for enhancing the diffraction differentiation of the exposed and unexposed portions of the resist preferably: 1) exhibit a large change of absorbance or index of refraction in the 300-900 nm wavelength range upon any chemical change in the photoresist, which would indicate photo or thermal processing had taken place, 2) be soluble in photoresist matrix, 3) not absorb in the 248, 193, or 13 nm wavelength range, and 4) not interfere with the diffusion and de-protection reaction mechanism during the lithography process. Other known techniques of enhancing the diffraction contrast between exposed or unexposed, chemically treated or not chemically treated, and/or low versus high concentration of a specific component of the resist can be used.

Referring to FIG. 4, the wafer (not shown) proceeds to the post exposure bake 412 process step where the wafer structure may be diffraction enhanced in the optical sensitivity enhancer 401 and measured in the metrology cluster 420. After the post exposure bake 412 process step, the wafer goes through the development 414 process step where the wafer structure may be diffraction enhanced in the optical sensitivity enhancer 401 and measured in the metrology cluster 420. The exposure 410, post exposure bake 412, and development 414 process steps may all be performed in one fabrication cluster device that also includes the optical sensitivity enhancer 403 and the metrology cluster 420.

Figure 5:
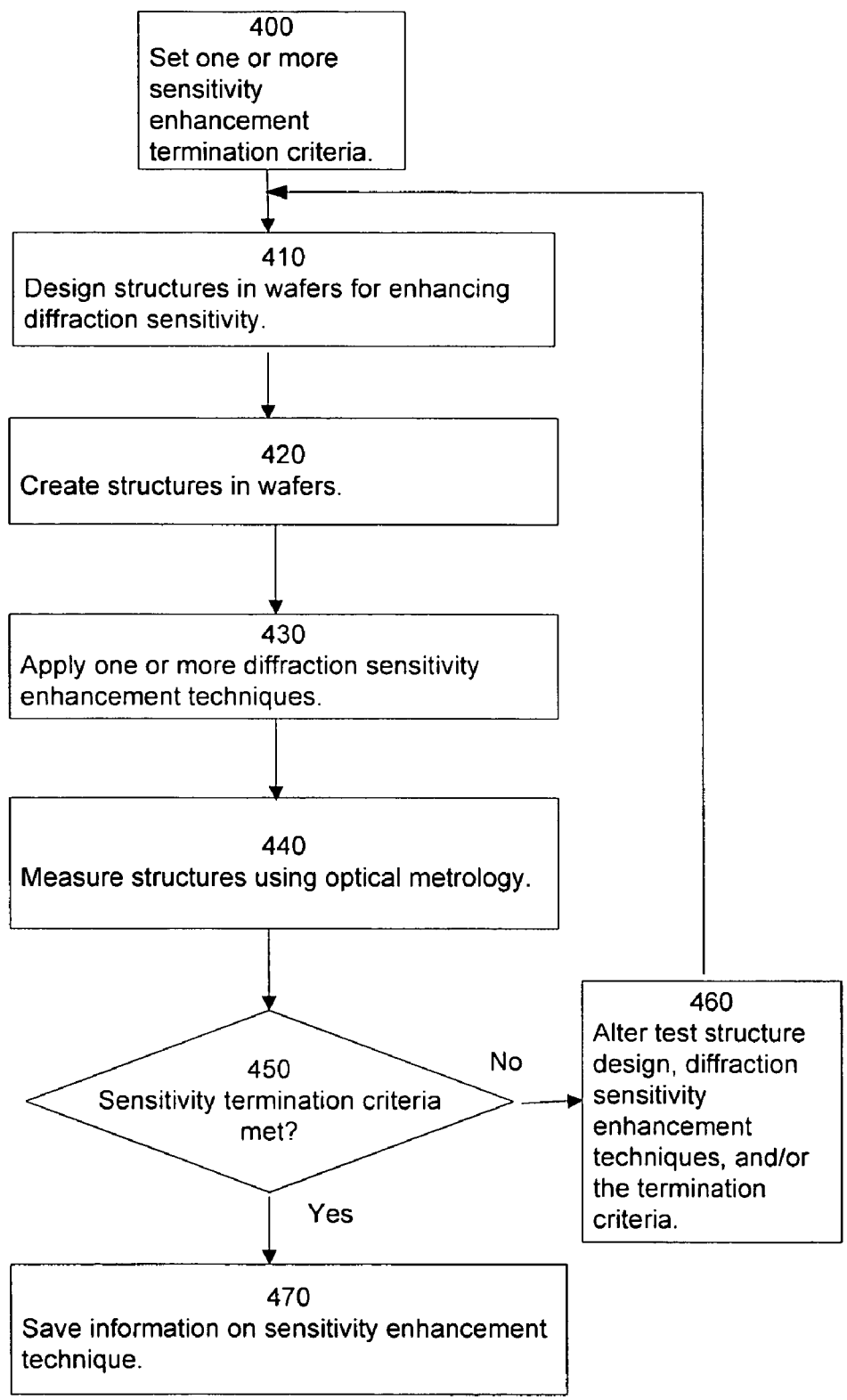
FIG. 5 is an exemplary flowchart for selecting one or more diffraction sensitivity enhancement of wafer structures for optical metrology.

For the rest of the specifications, the term unpatterned structure refers to areas of the wafer that includes layers and do not have structures such as posts, contact holes, gratings or the like. The term patterned structures refers to areas of the wafer that includes layers and structures such as posts, contact holes, gratings or the like. FIGS. 5, 6, and 7 are exemplary flowcharts of steps to 1) select one or more diffraction sensitivity enhancement techniques of wafer structures for optical metrology, 2) select a profile model of the patterned structure after the one or more diffraction signal sensitivity enhancement techniques have been applied, and 3) optimize the optical metrology model of the patterned structure treated with the selected one or more diffraction sensitivity enhancement techniques and the selected profile model of the patterned structure.

FIG. 5 is an exemplary flowchart for selecting one or more diffraction sensitivity enhancement techniques for wafer structures for optical metrology. In step 400, one or more sensitivity enhancement termination criteria are set. The termination criteria may include a cost function between the diffraction signals of the patterned versus the unpatterned portions of the wafer structures. For example, a termination criterion may be a cost function of 4.0 or higher between the diffraction signals of the patterned versus the unpatterned portion of the structure. Another criterion may be a low goodness of fit, 0.75 or lower for example. The other statistical measures of comparisons between two curves may be used such as sum squared error (SSE) or the log of SSE, and the like. In step 410, structures in the wafer are designed for testing enhancement of diffraction sensitivity. The structures may be located in the scribe line or in the die or in special test areas of the wafer. The patterned structures include portions that are treated and portions untreated by the treatment process. For example, if the treatment process is photolithography, the patterned structures would include exposed (treated) and unexposed (untreated) portions. If the treatment process is a patterned etch process, the patterned structure includes a treated portion not covered by the resist and an untreated portion covered by the resist, while the unpatterned structure is covered by the resist.

Referring to FIG. 5, in step 420, the structures designed for testing enhancement of diffraction sensitivity are created. For example, depending on when the patterned structure are being measured in the photolithography process, the patterned structure created may be the patterned structure after exposure, after post exposure baking, or after the development process. In step 430, one or more diffraction enhancement techniques are applied. As mentioned above, a diffraction enhancement technique is a process where one or more devices or processes adjust the properties or material content of the patterned structure such that the treated and untreated portions of the structure provide different diffraction characteristics. Also, as mentioned above, a molecule or compound that meets the diffraction enhancing requirements of the application is applied to the patterned structure to enhance the contrast of the diffraction characteristics of the treated and untreated portions. More specifically, the application of certain dyes to exposed but undeveloped wafers in a photolithography process has been proven to enhance the contrast of the diffraction characteristics of the exposed versus unexposed portions of the wafer. In one embodiment, a fluorescent acridine dye that is soluble in cyclohexanone is used to enhance the differentiation of the diffraction characteristics of the exposed versus unexposed portions of the wafer. In one embodiment, several dyes including Rhodamine B, Fluorescein, Coumarin 6, and 4-hydroxy-3-methoxy-cinnamaldehyde may be used to enhance the differentiation of the diffraction characteristics of the exposed versus unexposed portions of the wafer. For a detailed description of the use of dyes for diffraction enhancements, refer to Cameron, et al., "Photoacid Generation in Chemically Amplified Resists: Elucidation of Structural Effects of Photoacid Generators using New Acid Sensitive Dyes for Monitoring Acid Generation", SPIE Vol. 3333, pg. 680. For a description of the use of dyes that detect acid only after the post exposure bake process step, refer to Kunihiro Ichimura, et al., "Photoacid-catalysed pigmentation of dyestuff precursors enhanced by acid amplifiers in polymer films", J. Mater. Chem., 2004, 14, 1164-1172.

In another embodiment, the enhancement technique includes the use of a dopant in an implantation process. A patterned masking material may protect underlying regions of a semiconductor substrate from undergoing a physical or chemical change during an ion implantation process. The patterned masking material may also undergo a physical or chemical change during the processing. The physical or chemical changes to the masking material during processing may change the optical properties of the material. For a detailed description of ion implantation as a diffraction enhancement technique, refer to refer to U.S. Pat. No. 6,462,817, METHOD OF MONITORING ION IMPLANT IN EXAMINATION OF AN OVERLYING MASKING MATERIAL, by Strocchia-Rivera, filed on May 12, 2000, and is incorporated in its entirety herein by reference.

Still referring to FIG. 5, in step 440, the created structures are measured using optical metrology. Using the lithography example, a first diffraction signal is measured off an unpatterned area of the wafer, which may be in the scribe line or in the die or in a special test area. A second diffraction signal or signals are measured off the created test structures using the same optical metrology device. The created test structures may be in the scribe line, in a special test area or in the die. As mentioned above, the patterned area includes structures that have the exposed and unexposed portions, and where one or more diffraction sensitivity enhancement techniques have been applied, Thus, a first diffraction signal is measured off the unpatterned structures of the wafer, and a second diffraction signal is measured off the patterned structures containing the exposed and unexposed portions of the patterned structure. The metrology device may be a reflectometer, ellipsometer, or the like. If more than one second diffraction signals are measured, a statistical average of the signals may be derived.

In step 450, the sensitivity enhancement value is calculated and compared with the set sensitivity enhancement termination criteria. If goodness of fit is set as a sensitivity enhancement termination criterion, the goodness of fit between the first diffraction signal and the second diffraction signal is calculated and compared to the set goodness of fit.

If the one or more sensitivity enhancement criteria are not met, the wafer structure design is altered, different diffraction enhancement techniques are applied, a different metrology device is used, and/or the one or more termination criteria are altered 460. Steps 410, 420, 430, 440, 450, and 460 are iterated until the one or more termination criteria are met. If the one or more sensitivity enhancement criteria are met, in step 470, information on the one or more diffraction sensitivity enhancement technique is saved. In the photolithography example, the information includes the type of dyes and other chemicals used, physical and chemical attributes of the dye, and the like.

Figure 6A:
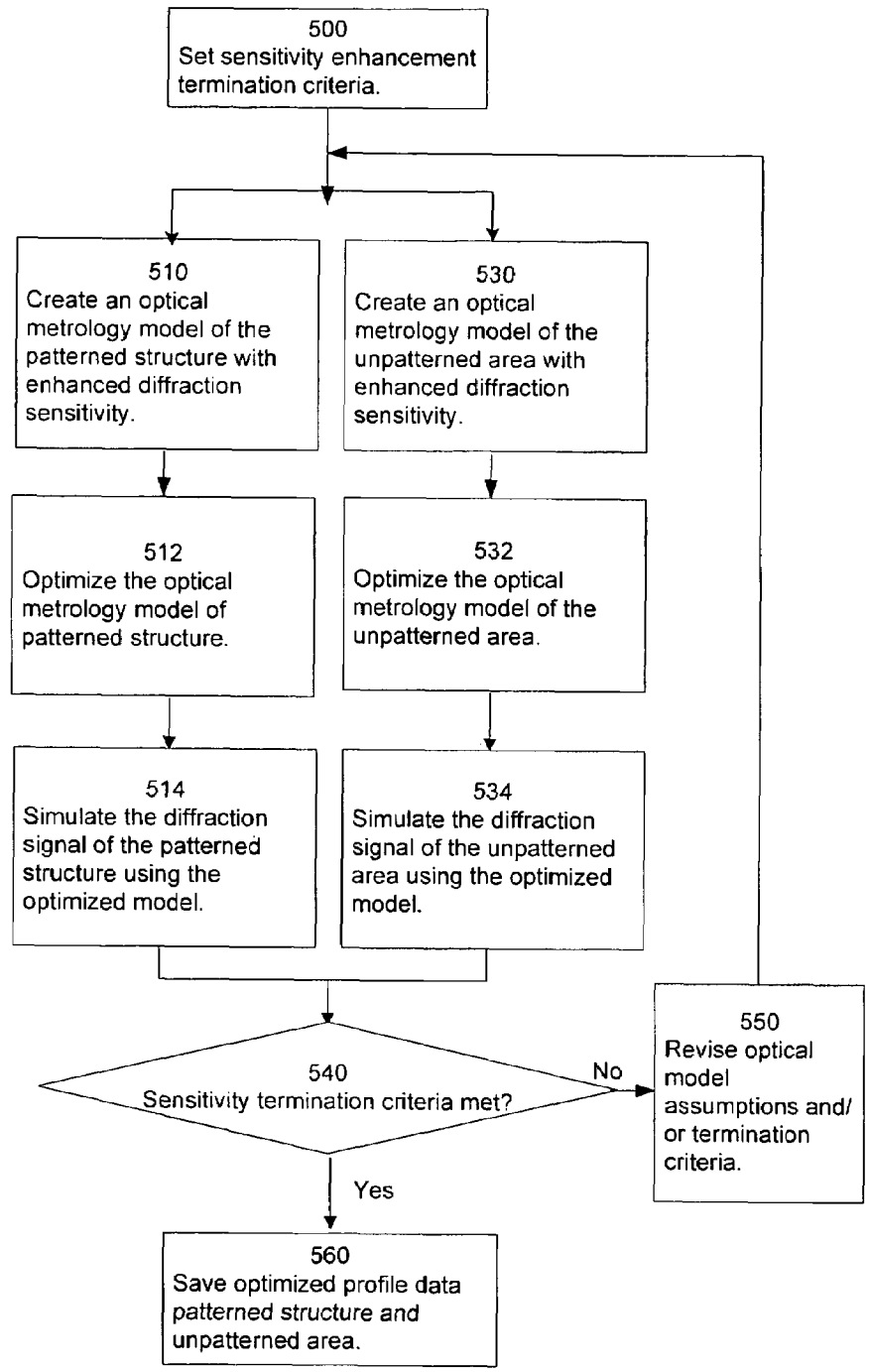
FIG. 6A is an exemplary flowchart of the modeling of patterned and unpatterned wafer structures with enhanced diffraction signal sensitivity.
Figure 7:
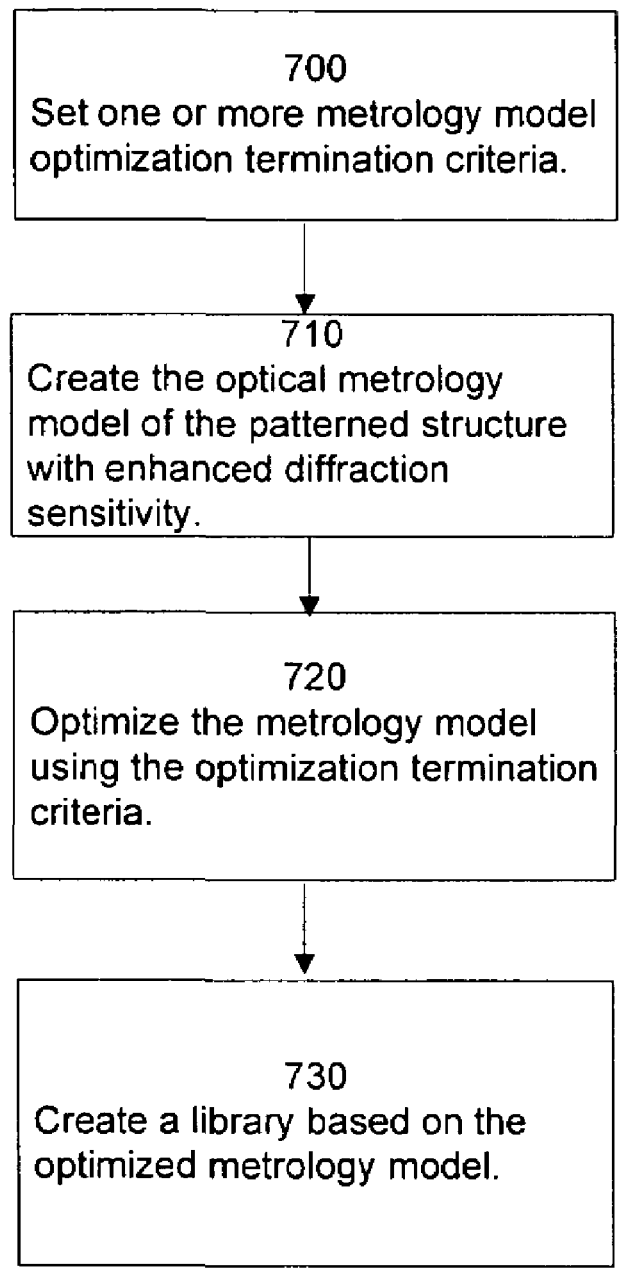
FIG. 7 is an exemplary flowchart for creating a library for determination of profile parameters of wafer structures with diffraction signal sensitivity enhancement.

FIG. 6A is an exemplary flowchart of the modeling of patterned and unpatterned wafer structures with enhanced diffraction signal sensitivity. In step 500, the one or more sensitivity enhancement termination criteria are set. Following step 500 are two parallel tracks of steps: steps 510, 512, and 514 for creating and optimizing an optical metrology model of the patterned structure, and steps 530, 532, and 534 for creating and optimizing an optical metrology model of the unpatterned structure.

In step 510, an optical metrology model is created for the patterned structure that is enhanced with the selected one or more diffraction sensitivity enhancing techniques, such as the sensitivity enhancing techniques selected in the method depicted in FIG. 5. Creation of the model includes characterization of the wafer structure profile. The wafer structure profile being characterized is the structure profile that exists after a process step. In the photolithography example, it is the structure profile after exposure, after post exposure bake, or after development. If the treatment process is etching, then the wafer structure profile being characterized is the structure profile that exists after a process step such as etching with the first etchant, cleaning, etching with the second etchant, and the like. As mentioned above, the patterned structure may comprise combinations of islands, contact holes, trenches, vias, line-and-space, and the like. The structure may be concave or convex in shape or combination of both. For a detailed description of modeling two-dimensional repeating structures, refer to U.S. patent application Ser. No. 11/061,303, OPTICAL METROLOGY OPTIMIZATION FOR REPETITIVE STRUCTURES, by Vuong, et al., filed on Apr. 27, 2004, and is incorporated in its entirety herein by reference.

In step 512, the optical metrology model of the patterned structure with enhanced diffraction sensitivity is optimized. A set of optimization parameters is selected for the profile model of the patterned structure and other metrology model variables using one or more input diffraction signals and one or more parameter selection criteria. The selected profile model and the set of model optimization parameters are tested against the one or more termination criteria. The process of selecting a profile model, selecting a set of optimization parameters, and testing the selected profile model and set of optimization parameters is performed until the one or more termination criteria are met. Optimization for profile model and profile model parameter selection, with the other metrology model variables, such as device, structure material, and simulation technique variables, setting selected variables to fixed values, is described in U.S. patent application Ser. No. 10/206,491 titled "Model And Parameter Selection For Optical Metrology", filed on Jul. 25, 2002, which is incorporated herein by reference in its entirety.

In step 514, a simulated diffraction signal is generated for the optical metrology model of the patterned structure. Simulation of the diffraction signal may be done using numerical analysis techniques such RCWA, Fresnel method, finite method, and the like. The effect of diffraction enhancement application is integrated into the simulation calculation. The simulated diffraction signal may be expressed as reflectance as a function of wavelength if a reflectometer is used, and ellipsometric values as a function of angle of incidence if an ellipsometer is used.

Still referring to FIG. 6A, in step 530, the optical metrology model of the unpatterned structure with enhanced diffraction sensitivity is created. The technique used is similar to those used in step 510. In step 532, the created optical metrology model is optimized in a similar manner as in step 512. In step 534, a simulated diffraction signal is generated for the optical metrology model of the unpatterned structure using the same method as in step 514. The simulated diffraction signal may be expressed as reflectance as a function of wavelength if a reflectometer is used, and ellipsometric values as a function of angle of incidence if an ellipsometer is used.

In step 540, the simulated diffraction signals off the unpatterned and the patterned structures are compared to determine the value of the sensitivity enhancement termination criteria. If the sensitivity enhancement termination criteria are not met, the optical metrology model parameters of the patterned and unpatterned structures and/or the termination criteria are revised and steps 510 to 550 are iterated until the termination criteria are met. Otherwise, in step 560, the profiles of the patterned and unpatterned structures are saved. It should be noted that similar methods apply to other fabrication processes, such as etching or chemical or physical vapor deposition.

Figure 6B:
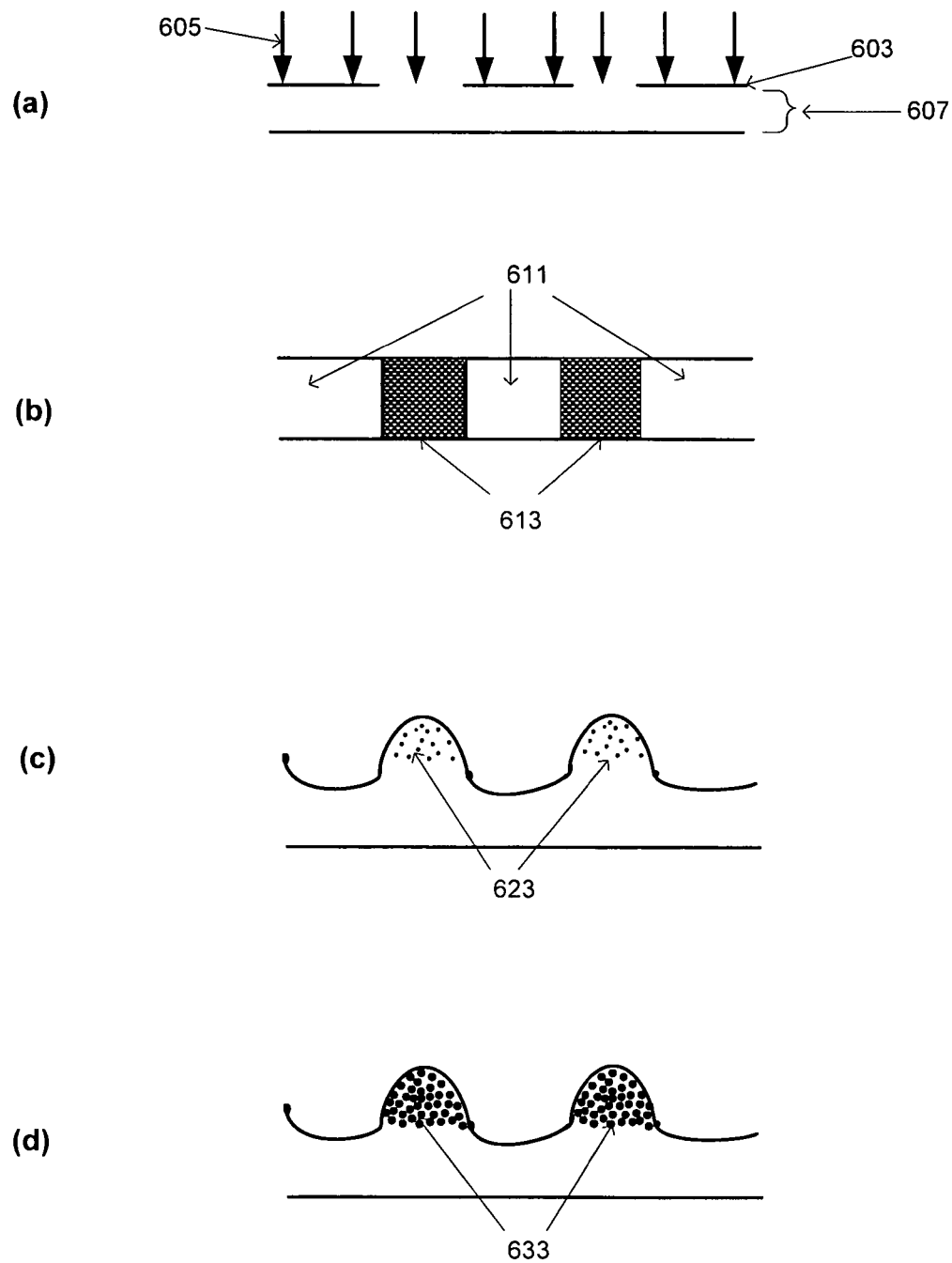
FIG. 6B is an architectural diagram of a photolithography structure depicting optical sensitivity enhancement of wafer structures for optical metrology.

FIG. 6B is an architectural diagram of exemplary photolithography structure profiles depicting optical sensitivity enhancement of wafer structures for optical metrology. More specifically, in FIG. 6B, (a) shows a beam 605 directed to a mask 603 above a photoresist 607. Portions of the beam 605 expose the photoresist 607 while other portions of the beam are stopped by the mask 603. Referring to (b) of FIG. 6B, the top-view of the mask shows the exposed 613 and unexposed 611 portions of the photoresist. Referring to (c) of FIG. 6B, a cross-sectional view of the structure shows the exposed portion of the photoresist 623 undergoing chemical transformation. Referring to (d) of FIG. 6B, the cross-sectional view of the structure shows the exposed portion of the photoresist 633 where a diffraction enhancement technique was applied. In one embodiment, the diffraction enhancement technique includes using a compound or a molecule that has the properties described above. In another embodiment, as mentioned above, a fluorescent acridine dye that is soluble in cyclohexanone is used to enhance the differentiation of the diffraction characteristics of the exposed versus unexposed portions of the structure. Also, as mentioned above, application of one or more diffraction enhancement technique may be done in other wafer fabrication processes such as in an etch or physical vapor deposition process.

FIG. 7 is an exemplary flowchart for optimizing the optical metrology model of the patterned structure treated with the selected one or more diffraction sensitivity enhancement technique and the selected profile model of the patterned structure. In step 700, one or more metrology model optimization criteria such as goodness of fit and/or cost function are set. In step 710, the optical model for the patterned structure where the one or more diffraction enhancing techniques are applied is created. This metrology model includes characterization of the patterned structure profile, the material of the patterned structure, the one or more diffraction enhancing techniques applied, and the metrology device. The patterned structure profile may be the profile selected in the method depicted in FIG. 6A. Alternatively, the patterned structure profile may be obtained from process simulation using software such as PROLITH™ and the like or from empirical or historical data using the same structure recipe. The diffraction enhancing technique may be selected using the method depicted in FIG. 5.

Referring to FIG. 7, in step 720, the patterned structure optical metrology model is optimized using measured diffraction signals off the patterned structure treated with the selected one or more diffraction sensitivity enhancement technique. For a detailed description of modeling two-dimensional repeating structures, refer to U.S. patent application Ser. No. 11/061,303, OPTICAL METROLOGY OPTIMIZATION FOR REPETITIVE STRUCTURES, by Vuong, et al., filed on Apr. 27, 2004, and is incorporated in its entirety herein by reference. In step 730, the optimized metrology model is used to create a library of pairs of simulated diffraction signals and corresponding profile parameters. In another embodiment, a machine language system is trained with pairs of simulated diffraction signals and corresponding profile parameters. For the description of creation and use of a trained machine language system, refer to U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

Figure 8:
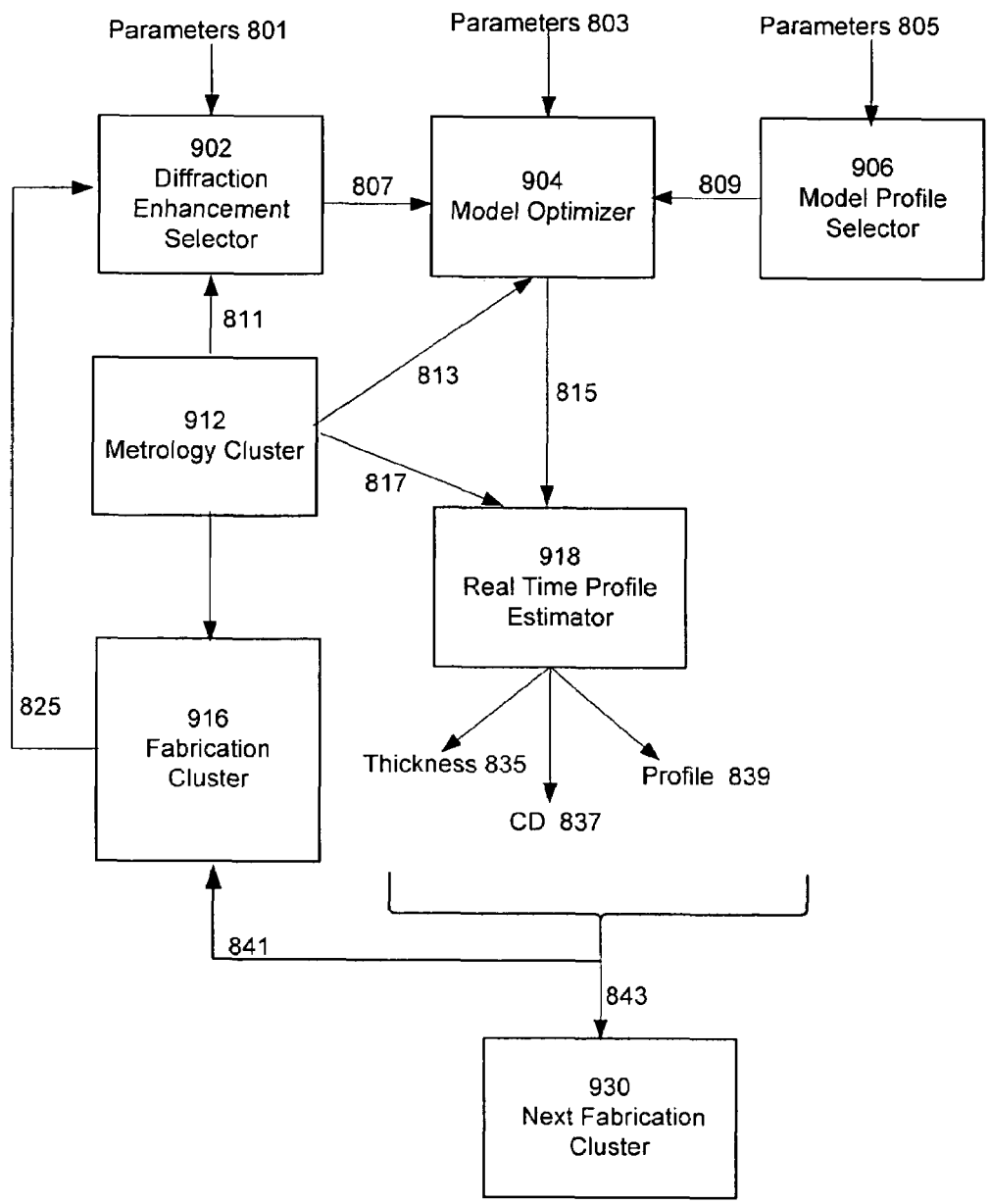
FIG. 8 is an exemplary architectural diagram of a real time profile estimator.

FIG. 8 is an architectural diagram illustrating an exemplary embodiment utilizing diffraction signal enhancement in a real-time CD estimator application. Using input parameters 801 setting the termination criteria, such as goodness of fit and/or cost function, for the optimization, a diffraction enhancement selector 902 is coupled to a fabrication cluster 916 and to a metrology cluster 912. One or more diffraction enhancement techniques are applied to a wafer structure (not shown) in the fabrication cluster 916. After each diffraction enhancement technique is applied, information about the diffraction enhancement technique 825 is sent to the diffraction enhancement selector 902. A patterned structure and an unpatterned structure are measured before and after application of the diffraction enhancement technique in the metrology cluster 912. The diffraction signals 811 obtained from measuring the patterned and unpatterned structures are transmitted to the diffraction enhancement selector 902 to test if the termination criteria are met. If the termination criteria are met, data about the diffraction enhancement technique 807 are transmitted to the model optimizer 904.

Using input parameters 805 to set the termination criteria such as goodness of fit and/or cost function, a model profile selector 906 selects a profile model of the wafer structure (not shown) enhanced with the one or more diffraction sensitivity enhancing techniques that meets the termination criteria. The selected profile model 809 is transmitted to the model optimizer 904. Using the transmitted diffraction enhancement technique 807 selected by the diffraction enhancement selector 902, the profile model 809 selected by the model profile selector 906, actual measured diffraction signals 813 from the metrology cluster 912, and the input parameters 803, the model optimizer 904 optimizes the optical metrology model to create an optimized optical metrology model that includes an optimized profile model of the structure.

Referring to FIG. 8, the real time profile estimator 918 uses the optimized profile model 815 from the model optimizer 904 and the measured diffraction signal 817 off the patterned structure to generate in real time the underlying film thickness 835, the CD and the profile 839 of the patterned structure. Feedback information 841 about the patterned structure such as CD 837 and data about the profile 839 may be transmitted to the fabrication cluster 916 for automated process control and equipment control. For example, a CD 837 value may be used to adjust an etch variable in an etch cluster. Similarly, feed-forward information 843 may be transmitted to the next fabrication cluster 930 for automated process control and equipment control.

Figure 9:
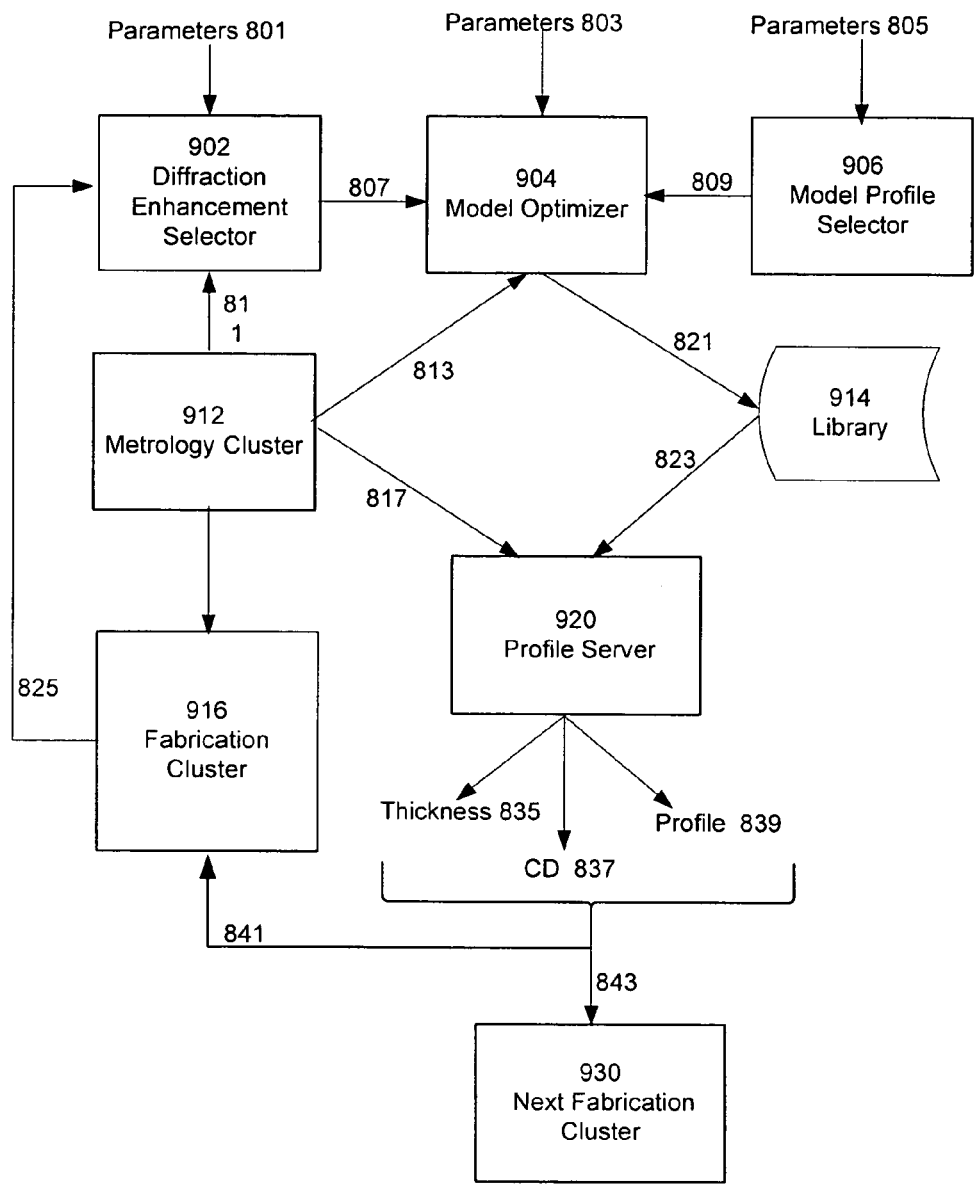
FIG. 9 is an architectural diagram of an exemplary embodiment for creating and using a library of simulated diffraction signals and profiles.

FIG. 9 is an architectural diagram of an exemplary embodiment for creating and using a library of simulated diffraction signals and profiles. The configuration of FIG. 9 is similar to FIG. 8 with two exceptions. First, the model optimizer 904 creates a library 914 comprising pairs of profiles and corresponding simulated diffraction signals. Second, instead of a real time profile estimator used in FIG. 8, a profile server 920 uses the library 914 and the measured diffraction signals 817 to generate the underlying film thickness 835, the CD and the profile 839 of the patterned structure. As mentioned above, alternatively, the profile server 920 may use a trained machine language system to generate the underlying film thickness 835, the CD and the profile 839 of the patterned structure.

As mentioned above, the diffraction enhancement techniques may include a chemical process, a mechanical process, or a combination of both. The diffraction enhancement technique may be done in one step such as application of a dye or in a series of steps such as various types of physical or chemical vapor deposition processes. Measurement of the diffraction signal may be done with reflectometers, ellipsometers, or hybrid devices.

In particular, it is contemplated that functional implementation of the present invention described herein may be implemented equivalently in hardware, software, firmware, and/or other available functional components or building blocks. Other variations and embodiments are possible in light of above teachings, and it is thus intended that the scope of invention not be limited by this Detailed Description, but rather by Claims following.

We claim:

1. A method of optimizing diffraction sensitivity of structures in a wafer for optical metrology, the wafer having a patterned structure and an unpatterned structure, the method comprising:
   a) setting one or more diffraction sensitivity enhancement termination criteria;
   b) creating a patterned structure on a wafer using one or more fabrication treatment processes, the patterned structure having a treated and an untreated portion;
   c) applying one or more diffraction sensitivity enhancement techniques to the patterned structure, wherein the one or more diffraction sensitivity enhancement techniques adjust one or more properties of the patterned structure to enhance diffraction contrast between the treated portion and untreated portion of the patterned structure;
   d) obtaining a first diffraction signal measured off the unpatterned structure on the wafer using an optical metrology device;
   e) obtaining a second diffraction signal measured off the patterned structure on the wafer using the optical metrology device;
   f) calculating a diffraction sensitivity enhancement value using the first and second diffraction signals; and
   g) comparing the calculated diffraction sensitivity enhancement values to the set one or more diffraction sensitivity enhancement termination criteria.

2. The method of claim 1 further comprising:
   h) if the one or more diffraction sensitivity enhancement termination criteria are not met, altering the one or more diffraction sensitivity enhancement techniques applied to the patterned structure and/or altering the one or more diffraction sensitivity enhancement termination criteria and iterating steps (b), (c), (d), (e), (f), (g), and (h) until the one or more diffraction sensitivity enhancement termination criteria are met.

3. The method of claim 1 wherein the one or more diffraction sensitivity enhancement termination criteria comprises a cost function between the first diffraction signal and the second diffraction signal and/or a goodness of fit between the first diffraction signal and the second diffraction signal.

4. The method of claim 1 wherein the one or more fabrication treatment processes include a photolithography fabrication step.

5. The method of claim 4 where the photolithography fabrication step includes placing a mask above a photoresist and exposing the photoresist to light.

6. The method of claim 5 wherein the photoresist includes a diffraction enhancing chemical.

7. The method of claim 1 wherein the one or more diffraction sensitivity enhancement techniques comprises application of a dye to the patterned structure.

8. The method of claim 1 wherein the one or more diffraction sensitivity enhancement techniques comprise one or more processes that alter the material content of the patterned structure.

9. The method of claim 1 wherein the one or more diffraction sensitivity enhancement techniques comprise one or more processes that alter the material composition of the patterned structure.

10. The method of claim 1 wherein the one or more diffraction sensitivity enhancement techniques comprise one or more processes that alter the physical characteristics of the patterned structure.

11. The method of claim 1 wherein the one or more fabrication treatment processes include an etching fabrication step.

12. The method of claim 1 wherein the one or more fabrication treatment processes include an ion implant fabrication step.

13. A method of modeling structures for optical metrology, the structures including a patterned structure and an unpatterned structure, the method comprising:
   a) setting one or more diffraction sensitivity enhancement termination criteria;
   b) creating a first optical metrology model corresponding to the unpatterned structure;
   c) generating a first simulated diffraction signal for the unpatterned structure using the first optical metrology model;
   d) creating a second optical metrology model corresponding to the patterned structure, wherein the patterned structure has a treated portion and an untreated portion, and wherein one or more properties of the patterned structure was adjusted using one or more diffraction sensitivity enhancement techniques to enhance diffraction contrast between the treated portion and the untreated portion of the patterned structure;
   e) generating a second simulated diffraction signal for the patterned structure using the second optical metrology model;

f) calculating a diffraction sensitivity enhancement value using the first and second simulated diffraction signals; and g) comparing the calculated diffraction sensitivity enhancement values to the set one or more diffraction sensitivity enhancement termination criteria.

14. The method of claim 13 wherein the one or more diffraction sensitivity enhancement techniques comprise application of a dye to the patterned structure.

15. The method of claim 13 wherein the one or more diffraction sensitivity enhancement techniques comprise one or more processes that alter the material content of the patterned structure.

16. The method of claim 13 wherein the one or more diffraction sensitivity enhancement techniques comprise one or more processes that alter the material composition of the patterned structure.

17. The method of claim 13 wherein the one or more diffraction sensitivity enhancement techniques comprise one or more processes that alter the physical characteristics of the structure.

18. The method of claim 13 wherein the one or more fabrication treatment processes include a photolithography fabrication step, an etch fabrication step, or an ion implant fabrication step.

19. A system for modeling a wafer structure processed with a diffraction enhancement technique, the system comprising:
- a fabrication cluster configured to apply one or more diffraction enhancement techniques to a patterned structure on a wafer and an unpatterned structure on the wafer;
- a metrology cluster configured to measure diffraction signals off the unpatterned and the patterned structures after the one or more diffraction enhancement techniques are applied;
- a diffraction enhancement selector configured to compare the diffraction signal off the unpatterned and the patterned structures after the one or more diffraction enhancement techniques are applied, determine if one or more diffraction enhancement termination criteria are met, and transmit the diffraction enhancement information; and
- a model optimizer coupled to the diffraction enhancement selector and the metrology cluster, the model optimizer configured to optimize an optical metrology model of the patterned structure using the diffraction enhancement information and a profile model of the patterned structure.

20. The system of claim 19 wherein the one or more diffraction enhancement techniques comprise application of a dye to the unpatterned and the patterned structures.

21. The system of claim 19 wherein the one or more diffraction sensitivity enhancement techniques comprise one or more processes that alter the material content of the patterned structure.

22. The system of claim 19 wherein the one or more diffraction sensitivity enhancement techniques comprise one or more processes that alter the material composition of the structure to enhance the contrast of diffraction characteristics of the treated versus untreated portions of the patterned structure.

23. The system of claim 19 wherein the one or more diffraction sensitivity enhancement techniques comprise one or more processes that alter the physical characteristics of the patterned structure to enhance the contrast of diffraction characteristics of the treated versus untreated portions of the patterned structure.

24. The system of claim 19 wherein the fabrication cluster includes a photolithography cluster, an etch cluster, a chemical deposition cluster, or a physical deposition cluster.

25. The system of claim 19 wherein the metrology cluster includes a reflectometer, an ellipsometer, and/or a hybrid optical metrology device.

26. The system of claim 19 further comprising a model profile selector configured to select a structure profile model that incorporates the effect of the one or more diffraction sensitivity enhancement techniques on the patterned structure.

27. The system of claim 19 further comprising a real time profile estimator configured to estimate a profile of the patterned structure based on the optimized optical metrology model and measured diffraction signals off the patterned structure.

28. The system of claim 27 further comprising a next fabrication cluster configured to use profile data for automated process control and equipment control.

29. The system of claim 19 further comprising a profile server configured to estimate the profile of the patterned structure based on a library of pairs of simulated diffraction signal and profile parameters and measured diffraction signals off the patterned structure.

30. The system of claim 29 further comprising a next fabrication cluster configured to use profile data for automated process control and equipment control.

31. A computer-readable storage medium containing computer executable code to select diffraction orders of a diffraction signal for use in optical metrology by instructing the computer to operate as follows:

a) setting one or more diffraction sensitivity enhancement termination criteria;

b) obtaining a first diffraction signal measured off an unpatterned structure on a wafer using an optical metrology device;

c) obtaining a second diffraction signal measured off an patterned structure on the wafer using the optical metrology device, wherein the patterned structure has a treated portion and an untreated portion, and wherein one or more properties of the patterned structure was adjusted using one or more diffraction sensitivity enhancement techniques to enhance diffraction contrast between the treated portion and the untreated portion of the patterned structure;

d) calculating a diffraction sensitivity enhancement value using the first and second diffraction signals; and e) comparing the calculated diffraction sensitivity enhancement values to the set one or more diffraction sensitivity enhancement termination criteria.

32. A computer-readable storage medium containing computer executable code to model wafer structures for use in optical metrology by instructing the computer to operate as follows:

a) setting one or more diffraction sensitivity enhancement termination criteria;

b) creating a first optical metrology model corresponding to the unpatterned structure;

c) generating a first simulated diffraction signal for the unpatterned structure using the first optical metrology model;

d) creating a second optical metrology model corresponding to the patterned structure, wherein the patterned structure has a treated portion and an untreated portion, and wherein one or more properties of the patterned structure was adjusted using one or more diffraction sensitivity enhancement techniques to enhance diffraction contrast between the treated portion and the untreated portion of the patterned structure;

e) generating a second simulated diffraction signal for the patterned structure using the second optical metrology model;

f) calculating a diffraction sensitivity enhancement value using the first and second simulated diffraction signals; and g) comparing the calculated diffraction sensitivity enhancement values to the set one or more diffraction sensitivity enhancement termination criteria.

* * * * *